Figure 1:
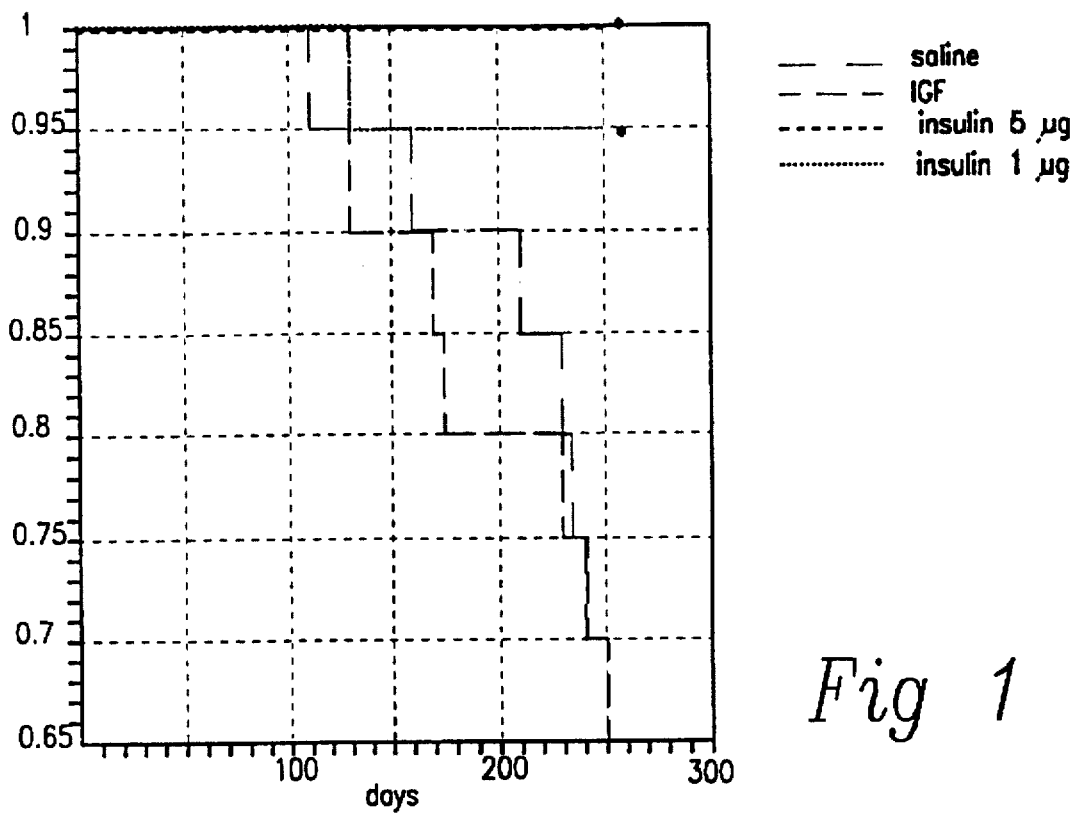

United States Patent [19]

Elliott

[11] Patent Number: 5,725,860
[45] Date of Patent: Mar. 10, 1998

[54] METHOD FOR REDUCING THE RISK OF DEVELOPING DIABETES

[75] Inventor: Robert Bartlett Elliott, Auckland, New Zealand

[73] Assignee: Auckland UniServices Limited, Auckland, New Zealand

[21] Appl. No.: 687,518

[22] PCT Filed: Mar. 6, 1995

[86] PCT No.: PCT/NZ95/00025

§ 371 Date: Aug. 7, 1996

§ 102(e) Date: Aug. 7, 1996

[87] PCT Pub. No.: WO95/24216

PCT Pub. Date: Sep. 14, 1995

[30] Foreign Application Priority Data

Mar. 7, 1994 [NZ] New Zealand ............................ 260046

[51] Int. Cl.$^6$ ............................ A61K 38/28; A61K 39/10
[52] U.S. Cl. ................................ 424/240.1; 514/2; 514/21
[58] Field of Search ......................... 514/2, 21; 424/240.1

[56] References Cited

FOREIGN PATENT DOCUMENTS

18157/83  8/1983  Australia .

OTHER PUBLICATIONS

Huang et al., Pediatric Research 18(2): 221–226 (1984).

Hollins et al., Clin. Exp. Immunol. 38: 127–134 (1979).

Hollins et al., Clin. Exp. Immunol. 31: 464–471 (1978).

Kolb et al., Diabetes Research 6: 21–27 (1987).

Primary Examiner—Jean C. Witz
Attorney, Agent, or Firm—Young & Thompson

[57] ABSTRACT

The incidence of the autoimmune disease, diabetes mellitus, is well controlled in the nude-obese-diabetic (NOD) mouse model using injections of the A chain fragment (or parts thereof) of the insulin molecule as an antigen in combination with killed cells (or parts thereof) of *Haemophilus pertussis*, acting as an adjuvant. This leads to the convenient prevention of diabetes in humans using the common "Triple vaccine" (DPT) diphtheria/whooping cough/tetanus vaccine (or versions thereof) in combination with A chain fragment of insulin. This mixture can be given to an at-risk population in which diabetes is expected to occur at an abnormally high rate, or it can be given to the entire population.

7 Claims, 3 Drawing Sheets

5,725,860

METHOD FOR REDUCING THE RISK OF DEVELOPING DIABETES

FIELD OF THE INVENTION

This invention relates to the field of prevention of diabetes in humans and other mammals by vaccination, more particularly to prevention of type I or juvenile diabetes but also to prevention of at least some cases of adult diabetes and also to prevention of certain other autoimmune diseases.

BACKGROUND

Diabetes mellitus of the juvenile onset type is a relatively common and incurable disease believed to be caused by an autoimmune reaction against the beta cells of the islets of Langerhans in the pancreas. The beta cells, which are the only source of insulin, become the selected subjects of attack by components of the immune system as a result of sensitisation and are usually totally destroyed.

Diabetes is a nasty disease in that it is substantially incurable and typically requires daily injections of insulin for life in order to control the symptoms by replacing the secretions of the destroyed cells. Injections may not be available in poorer countries which often lack the means for such a treatment. Diabetes has an incidence (in its juvenile form, also known as Type I) of about 200 cases per year in New Zealand (population 3.2 million). Apart from the suffering as a result of the disease and as a result of the necessary dietary restrictions and the treatment itself (which is not without hazards) it is estimated that lifetime treatment of a juvenile diabetes case costs around NZ $1 million. A second form of diabetes—maturity onset diabetes—has an incidence of over 1 in 100 and some (perhaps 20%) of these cases are believed to be a late-onset type I diabetes of autoimmune origin.

Baeder et al (U.S. Pat. No. 5,321,009) advocates medication with rapamycin to modify the autoimmune response in patients with diabetes—this at least partially can reduce the dose of insulin required. Nevertheless it is a pragmatic and fundamental principle of medicine that immunisation is almost always preferable to medication. A method of protecting an individual from the appearance of diabetes could therefore be worth several hundred million dollars annually to a country having the population size of New Zealand.

OBJECT

It is an object of the present invention to provide an improved procedure for the prevention or alleviation of diabetes mellitus or one which will at least provide the public with a useful choice.

STATEMENT OF THE INVENTION

In one aspect the invention provides a composition for use in treatment of mammals, the composition comprising a mixture of an effective amount of an adjuvant and an effective amount of an antigen in a pharmaceutically acceptable carrier, wherein the adjuvant includes killed cells of *Haemophilus pertussis* or components thereof.

In a broad aspect the invention provides a composition for use in treatment of mammals affected by, or liable to be affected by, an auto-immune disease, the composition comprising a mixture of an effective amount of an adjuvant and an effective amount of an antigen in a pharmaceutically acceptable carrier, wherein the adjuvant includes killed cells of *Haemophilus pertussis* or components thereof.

In a related aspect the invention provides a composition for use in treatment of mammals affected by, or liable to be affected by the disease known as diabetes, the composition comprising a mixture of an effective amount of an adjuvant and a portion of an insulin molecule in an effective amount, in a pharmaceutically acceptable carrier, wherein the adjuvant includes killed cells of *Haemophilus pertussis* or components thereof.

Preferably the adjuvant also contains tetanus toxoid and diphtheria toxoid.

Preferably the adjuvant also contains antigenic material from *Haemophilus influenzae* type B.

Preferably the portion of the insulin molecule used comprises at least a portion of the A chain peptide of that molecule.

Preferably the entire A chain is used.

Optionally the portion of the insulin molecule used comprises at least a portion of the "A" chain, and a portion of the "B" chain.

In another broad aspect, the invention provides a method for the administration of the composition as described previously in this section, comprising its administration as one or more injections.

In a related aspect the invention provides a method as described previously in this section, wherein the insulin fragment and the adjuvant are not a mixture but are administered at separate sites.

In a related aspect the invention provides a method as described previously in this section, in which the dose rate for a human is in the range of from 50 micrograms (µg) to 20 milligrams (mg) of peptide per dose.

In a related aspect the invention provides a method as described previously in this section, in which the dose rate for a human subject is in the range of from 100 micrograms (µg) to 15 milligrams (mg) of peptide per dose.

In a related aspect the invention provides a method as described previously in this section, in which the dose rate for a human subject is from about 1 mg to about 10 mg per dose.

In a related aspect the invention provides a method as described previously in this section, in which the dose rate for a human subject is about 10 mg per dose.

In another broad aspect, the invention provides a method for causing protection in a mammal against damage caused by an auto-immune process comprising the administration of a mixture of an adjuvant based on killed cells of *Haemophilus pertussis* or components thereof, and an antigen, in a pharmaceutically acceptable carrier.

In a further broad aspect, the invention provides a method for causing protection in a mammal against damage to pancreatic islet beta cells comprising the administration of a mixture of an adjuvant and a portion of an insulin molecule including at least part of the "A" chain in a pharmaceutically acceptable carrier.

In a related aspect the invention provides a method for reducing the incidence of diabetes of the juvenile form in a population comprising the step of inoculating individuals with the composition as described previously in this section, without regard for individual risk.

In another related aspect the invention provides a method for reducing the incidence of diabetes in a population comprising the steps of identifying individuals having special risk of contracting diabetes and administering a composition as described previously in this section.

In a yet further broad aspect the invention provides a composition for causing protection against auto-immune damage to pancreatic islet beta cells comprising a mixture of an adjuvant and a portion of an insulin molecule, in a pharmaceutically acceptable carrier.

Preferably the adjuvant is one including killed cells of *Haemophilus pertussis* or components thereof.

More preferably the adjuvant also contains tetanus toxoid and diphtheria toxoid and preferably this is the mixture dispensed as "triple vaccine" or DPT.

Alternatively the adjuvant may be "quadruple vaccine" which also includes antigenic material from *Haemophilus influenzae* type B.

Preferably the portion of the insulin molecule used comprises the A chain peptide of that molecule.

Alternatively it may comprise a portion of the A chain.

As a further alternative it may comprise a portion of the A chain and a portion of the B chain.

Preferably the composition is administered as one or a series of subcutaneous injections.

Alternatively it may be given as separate insulin fragment, and adjuvant, at separate sites.

In another aspect the invention provides a method for causing protection against auto-immune damage to pancreatic islet beta cells comprising the administration of a mixture of an adjuvant and a portion of an insulin molecule in a pharmaceutically acceptable carrier.

Preferably the mixture is given at about one, three, and six months of age to humus at a dose rate in the range of from 10 µg to 20 mg of A chain peptide per individual.

Optionally, booster doses may be given from time to time.

In a related aspect the invention comprises a method for selecting persons at risk from diabetes and administering a prophylactic series of one or more inoculations as above.

Optionally, individuals may be selected for treatment according to predisposing factors, such as either having relatives with a history of diabetes, or relatives or the person in question having indications of raised antibodies against islet cells.

In an alternative aspect the invention comprises a method for protecting a population from diabetes mellitus of juvenile form by inoculating individuals without regard for individual risk.

PREFERRED EMBODIMENT

The following is a description of a preferred form of the invention, given by way of example only, with reference to the accompanying diagrams.

FIG. 1: shows the survival distribution function estimate for NOD mice injected with insulin, IGF1 or saline twice daily, 5 days per week, from 40 to 120 days.

Figure 2:
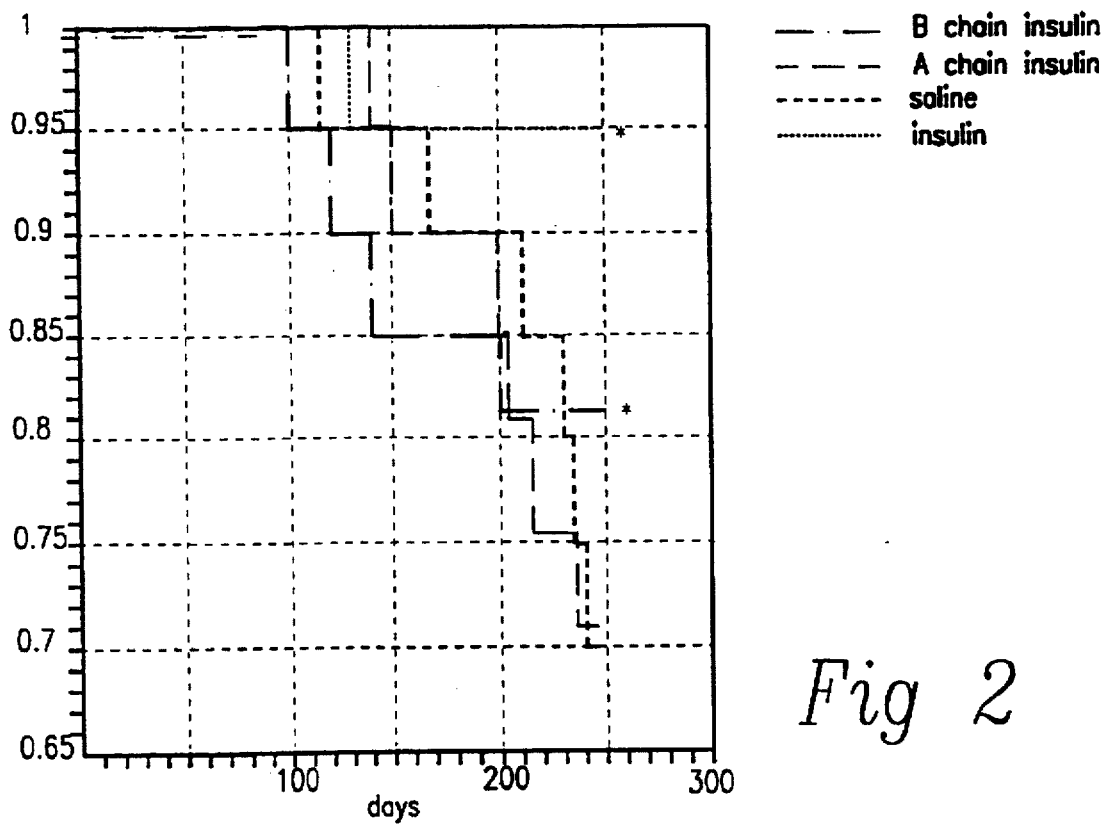

FIG. 2: shows a comparison of diabetes rates, using the survival distribution function estimate for NOD mice injected with 1 µg insulin, A-chain, or B-chain in saline, twice daily, 5 days per week, from 40 to 120 days.

Figure 3:
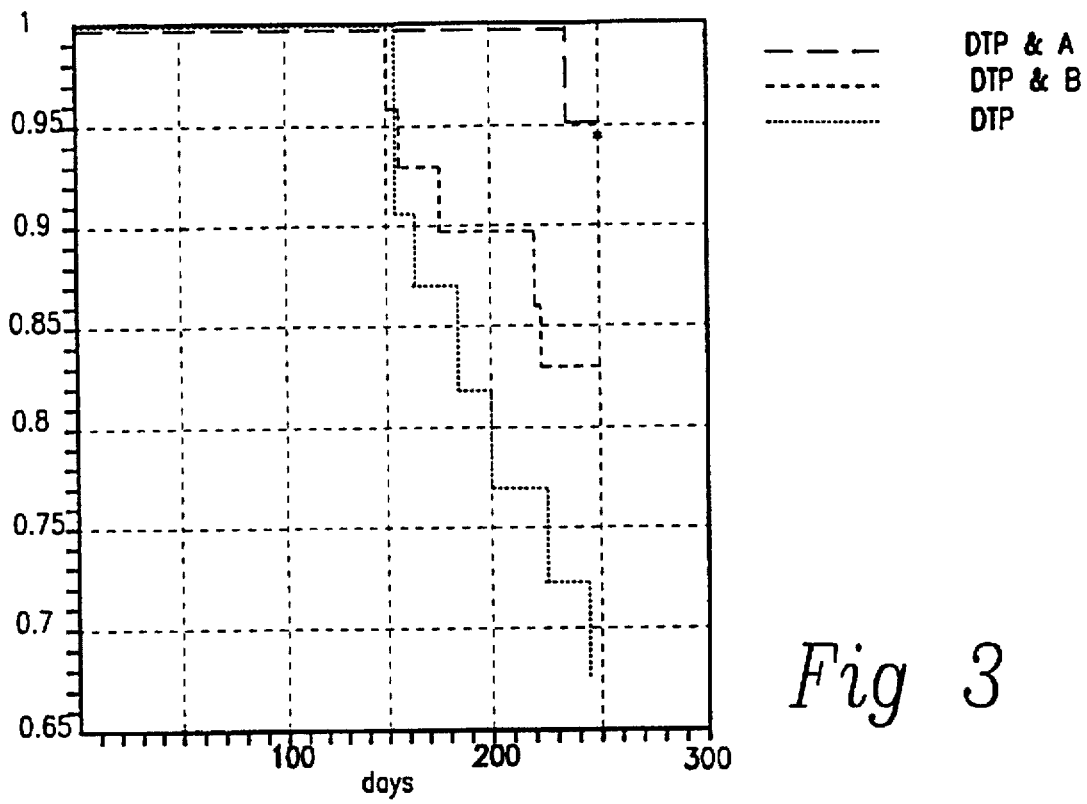

FIG. 3: shows the survival distribution function estimate for NOD mice injected with 100 µg A chain or B chain of insulin, with the adjuvant DTP, at 1,2 3, and 11 weeks of age.

Figure 4:
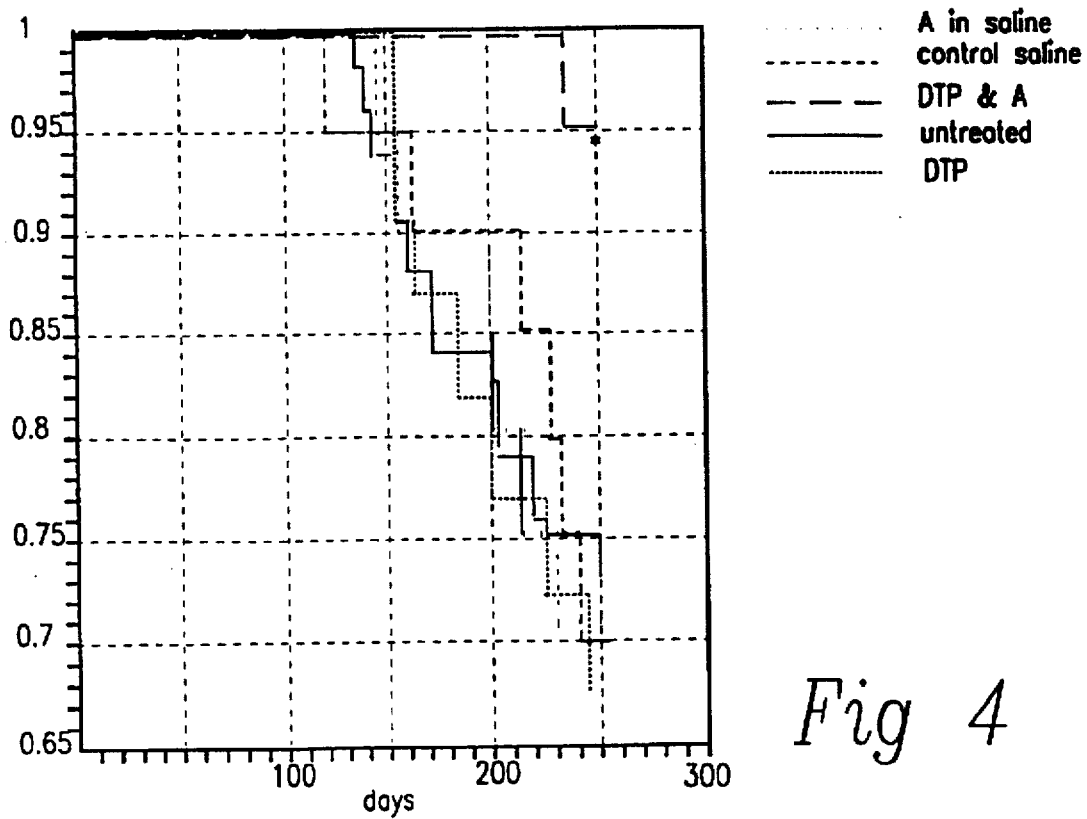

FIG. 4: shows the survival distribution function estimate for NOD mice injected with 100 µg A chain of insulin either in saline or with the adjuvant DTP.

Figure 5:
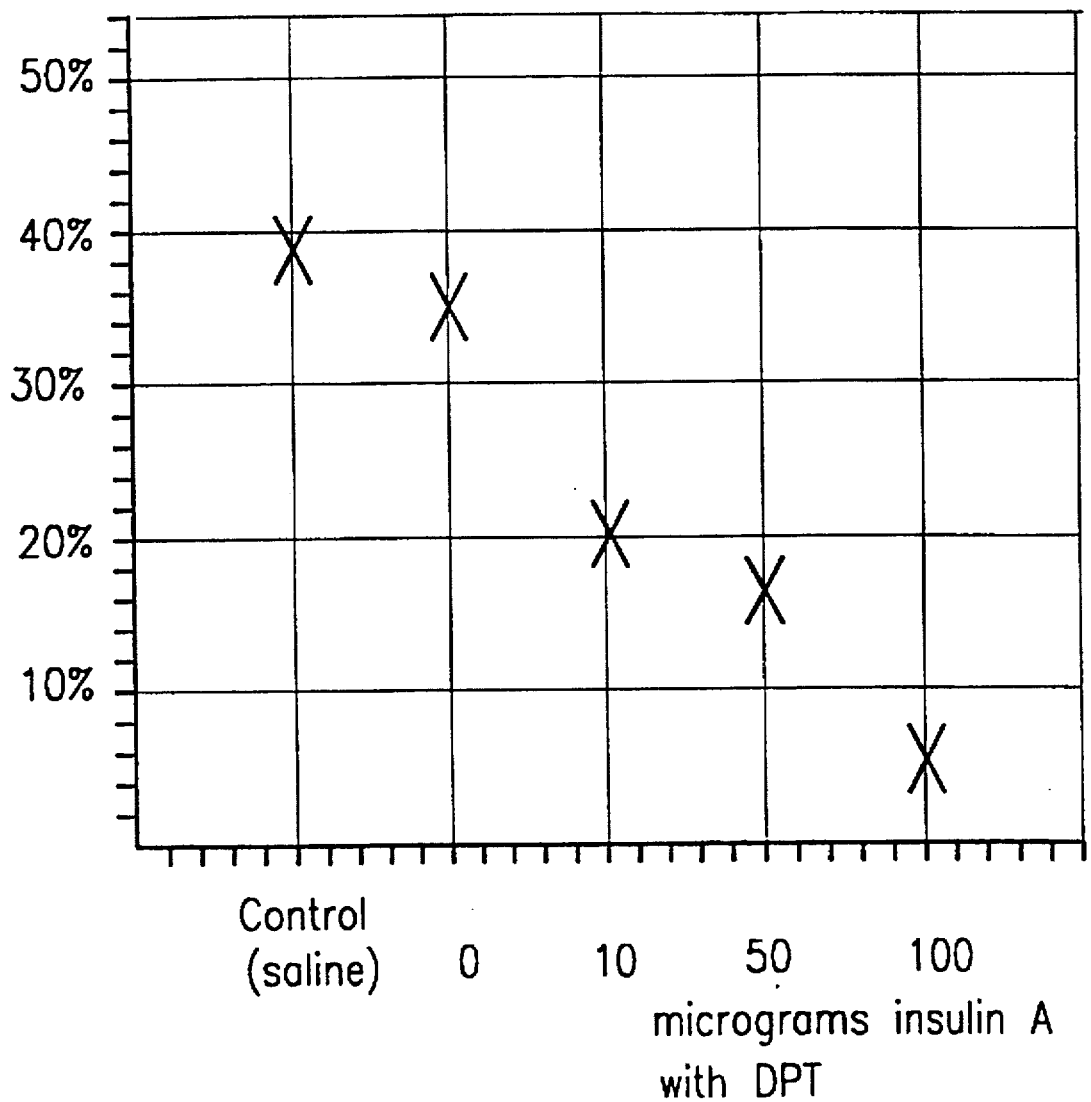

FIG. 5: shows a dose/response relationship for our preferred composition of DPT and A chain treatment.

It has surprisingly been found that treatment of mice belonging to the non-obese diabetic (NOD) strain carried out according to this invention has resulted in a high degree of prevention of the otherwise inevitable appearance of diabetes mellitus in these mice. This strain is generally believed to be a good model for human diabetes.

It is interesting to observe that the disease diabetes mellitus, in which a relative deficiency of the small protein insulin—a hormone—results in aberrations of the levels of circulating glucose can be prevented in a mammal by administering a composition intended to raise antibodies against insulin, or at least the "A" chain peptide of the molecule. Superficially, one might have expected such a treatment to further lower the levels of endogenous insulin. This effect appears to be particularly relevant to type I diabetes mellitus; an autoimmune disease.

In summary, an example treatment as described in the preferred embodiment comprises one or more injections with a mixture of the A chain of the insulin molecule (which fragment is substantially inactive, metabolically speaking) together with an adjuvant comprising "Triple vaccine" a widely used mixture of diphtheria toxoid, tetanus toxoid, and killed cells of *Haemophilus pertussis* (the microbe of whooping cough)—otherwise known as DTP as is commonly administered to children. This treatment appears to promote a protective form of immune response so that the otherwise inevitable autoimmune attack on the cells that produce insulin is not effective. As this mouse model is in most respects a close parallel of human diabetes it is expected that this treatment will also be effective in the prevention of human diabetes due to autoimmune activity in humans and a proposed treatment protocol for children is included.

EXPERIMENTAL EVIDENCE

Diabetes in the NOD mouse can be prevented or delayed significantly in its onset by the administration of insulin, prior to the usual time of onset of the spontaneous disease in this strain. See Atkinson et al (1990) *Diabetes* 39 933–937. It is far from clear how insulin exerts this protective effect, but among the theories put forward are the concepts that exogenous insulin reduces the metabolic activity of the B-cells, and thus reduces their susceptibility to immune attack (Aaen et al (1990) *Diabetes* 39 697–701, Sadelain et al (1990) *Diabetes* 39 583–589). Other mechanisms for the effect such as induction of tolerance by a variety of pathways have also been suggested (Steinman, L (1990) *Mol. Biol. Med.* 7 333–339). A third possibility is that greater growth of B cells might in some way be enhanced, with B-cell replication outstripping the destruction found in this model.

As the use of insulin itself may be hazardous in humans, we decided to test the ability of compounds which have some structural homology with insulin, to prevent diabetes. These substances included insulin—like growth factor (IGF1) the A and B chains of insulin, and a peptide derived from the B chain (approximately B9-20). Our A chain material was of bovine or porcine origin. Of course, human and porcine A chains are substantially identical.

GENERAL METHODS

Female NOD mice from our own colony were used throughout. About 40% of these mice develop diabetes as evidence by continuous glycosuria, hyperglycaemia, and diabetic symptoms between the ages of 115 and 250 days. The animals were kept in standard animal facilities and fed chow ad lib throughout. Females were weaned at 21 days and separated into cages, 3–4 to a cage. Where indicated in the results the individual animals were randomly allocated to these cages or the whole litter was thus randomly allocated. Animals were allocated to the particular treatment in groups of 20–24 (the number in 5 litters). Treatments were parenteral, by the subcutaneous route.

The DPT vaccine used was: lot 128870213 from the Swiss Serum and Vaccine Institute, Berne, Switzerland. The DT vaccine used was lot B 0427-07708 from CSL Ltd, Victoria, Australia. The T vaccine used was lot B 0486-28306 from CSL Ltd., Victoria, Australia.

Experiment 1 compared relatively low doses of Insulin, bovine A, and bovine B chains, and IGF-1 over an extended administration period.

Experiment 2 compared various forms of insulins with DPT using less frequent dose schedules.

Experiment 3 was set up to compare the levels of antibody to insulin "A" chains with the degree of protection obtained.

Experiment 4 was set up to make a dose-response curve for insulin A chain with DTP.

Experiment 5 was set up to ascertain which components of the adjuvant were particularly effective.

PARTICULAR EXPERIMENTS

Experiment 1

In a first series of experiments, animals were given the test substance dissolved in 'normal' saline as a subcutaneous injection twice a day on 5 consecutive days per week with a 2 day respite.

The treatment groups are as follows:

| Substance Given | Dose/Day 5 days/week | Commencement time | Duration of admin |
|---|---|---|---|
| Insulin | 2 μg | 40 days | 80 days |
| Insulin | 10 μg | 80 days | 80 days |
| Bovine B chain* | 2 μg | 40 days | 80 days |
| Bovine A chain* | 2 μg | 40 days | 80 days |
| IGF1 | 20 μg | 40 days | 80 days |

The onset of diabetes in the first series of experiments is presented as life tables (FIG. 1 and FIG. 2). Insulin in either of the three dose schedules used significantly prevented diabetes. Insulin A chain, B chain and IGF1 did not significantly alter the diabetes rate found in the control group.

Experiment 2

In a second series of experiments the substances were given in a timing schedule designed to approximate those used in humans for triple antigen immunizations (triple vaccine—DPT) adjusted for the difference in natural weaning times. The substances, and the dosing schedule are as follows:

| Substance Given | Dose | Timing of Administration |
|---|---|---|
| Insulin x + DPT | 2 μg | 7, 14, 21, 77 days |
| Porcine A chain + DPT | 10 μg | 7, 14, 21, 77 days |
| Porcine A chain + DPT | 50 μg | 7, 14, 21, 77 days |
| Porcine A chain + DPT | 100 μg | 7, 14, 21, 77 days |
| Porcine B chain + DPT | 100 μg | 7, 14, 21, 77 days |
| Porcine B 13–21 chain fragment + DPT | 100 μg | 7, 14, 21, 77 days |
| Control | | |

In the second series of experiments using a 100 μg dose, effective protection from diabetes was seen with only the insulin A chain in combination with DPT given in the neonatal or later schedules. A dose of 50 μg was only partially effective, and a dose of 10 μg was not effective. DPT alone or in combination with the B chain was not effective (FIG. 3 and FIG. 4).

Groups receiving insulin all showed high levels of insulin antibody, but those receiving the insulin derivatives or the control substances did not show antibody more than that expected from the background autoantibodies.

Diabetes outcome was measured by twice a week urine testing (Testape) Persistent heavy glycosuria for 3 consecutive days was invariably associated with gross hyperglycaemia and eventually diabetic symptoms. The animals were weighed during the administration of the substances. Animals which were not diabetic at 250 days were killed by an ethically approved method and the pancreas removed into Bouin's fixative. Blood samples were drawn terminally.

Each fixed pancreas was sectioned and stained with haematoxylin and eosin. These sections were assessed for islet changes by standard methods, comprising the following numerical ratings: 0=no insulitis, 1=minimal periislet infiltration, 2=marked periislet infiltration, 3=minimal intraislet infiltration, 4=marked intraislet infiltration. The scores were corrected to a maximum of 100, and at least 10 islets were observed.

Terminal serum was measured for insulin antibodies by a modification of a radioligand binding technique using 20 μl serum. The method is given in Vardi, P Dib SA Tuttleman M., Connelly J. E. et al. Diabetes 36 1286–1291 (1987).

| Animal # | A-chain DTP | Animal # | Controls score |
|---|---|---|---|
| 1 | 57 | 1 | 87 |
| 2 | 0 | 2 | 89 |
| 3 | 31 | 2 | 67 |
| 4 | 34 | 4 | 7 |
| 5 | 4 | 5 | 69 |
| 6 | 75 | 6 | 39 |
| 7 | 0 | 7 | 57 |
| 8 | 18 | 8 | 64 |
| 9 | 41 | 9 | 72 |
| 10 | 61 | 10 | 1 |
| 11 | 53 | 11 | 79 |
| 12 | 16 | 12 | 11 |
| 13 | 66 | 13 | 29 |
| 14 | 68 | 14 | 65 |
| 15 | 0 | 15 | 86 |
| 16 | 10 | 16 | 56 |
| 17 | 48 | | |
| 18 | 69 | | |
| 19 | 81 | | |
| 20 | 28 | | |
| MEANS | 38 | | 55 |
| Score > 50 | 8/20 | | 11/16 |

Evidently there was a reduction of infiltration in those animals that received the A-chain DTP treatment.

Experiment 3

In a third series of experiments, some evidence that the "A" chain of the insulin molecule is effective was provided. We measured the amount of antibody to "A" chain to be found (measured at 120 days) in a series of animals that had been treated with 10 or 50 or 100 μg doses of antigen/adjuvant as described elsewhere.

This table shows the EIA of A-chain antibodies related to diabetes outcome.

| # | OD Diabetic (+ or −) at (days) |
|---|---|
| 1 | 0 − (230) |
| 2 | 0 − (230) |
| 3 | 0 − (230) |
| 4 | 0 + (179) |
| 5 | 0 + (179) |
| 6 | 0.017 + (181) |
| 7 | 0.021 + (228) |
| 8 | 0.032 − (230) |
| 9 | 0.042 − (230) |
| 10 | 0.045 − (230) |
| 11 | 0.047 − (230) |
| 12 | 0.080 − (230) |
| 13 | 0.085 − (230) |
| 14 | 0.094 − (230) |
| 15 | 0.099 − (230) |
| 16 | 0.104 − (230) |
| 17 | 0.104 − (230) |
| 18 | 0.236 − (230) |

Conclusion

4/7 with OD<0.022 developed diabetes

0/11 with OD>0.031 did not.

4 insufficient serum—none developed diabetes by 230 days

Experiment 4

In a fourth series of experiments the dose of A-chain given to groups of about 20 animals (NOD mice) was varied, while keeping the amount of DTP constant, and the diabetes incidence at the end of the experiment at 250 days was compared with the dose. The substances and the outcome are as follows:

| Substance Given | Dose of A chain | Diabetes Outcome |
|---|---|---|
| Insulin A + DPT | 0 µg | 7/20 |
| Insulin A + DPT | 10 µg | 5/21 |
| Insulin A + DPT | 50 µg | 4/22 |
| Insulin A + DPT | 100 µg | 1/20 |
| saline only | | 9/23 |

It can be seen that there is a dose-response relationship or effect. This has been plotted in FIG. 5 as a dose-response curve (though an actual curved line has not been added). Note that an about 40% incidence is typical of untreated mice of this strain over this period.

Experiment 5

This experiment was designed to assess which component of the triple vaccine (DTP) appeared to have the effective adjuvant effect. In this series of experiments NOD female mice were injected in the same immunising dose as before, but using a diphtheria plus tetanus toxoid vaccine instead of the full DTP vaccine with and without the added insulin A-chain. The evolution of diabetes was then studied as before. At the end of the experiment, 9 out of 21 animals in both groups had diabetes, which is no different to the rate found in animals not receiving any form of vaccination. Similar results were obtained using tetanus toxoid alone, in lieu of the other adjuvants. No protection was afforded, whether or not A-chain was added to tetanus toxoid.

The conclusions we draw from this are that the pertussis vaccine is the active adjuvant in the mixed, triple vaccine, and that the diphtheria and tetanus vaccine are without effect. It also appears that A-chain itself, or in combination with diphtheria and/or tetanus vaccine is ineffective. The pertussis vaccine used was a "cellular" vaccine containing many defined, and some undefined components, and so we are unable to specify which component or components of the vaccine contain(s) the active principle. Indeed, diphtheria and/or tetanus vaccines may be required in addition as "co-factors". It may be relevant that for a long time pertussis toxin has been known to stimulate insulin secretion from the islets of Langerhans, probably through the "G protein" control sequence.

| Substance Given | Dose | Diabetes Outcome |
|---|---|---|
| DT alone | 0 µg | 7/21 |
| Insulin A + DT | 100 µg | 7/21 |
| Insulin A + DPT | 100 µg | 1/21 |

It appears likely that the useful effect of DTP as an adjuvant resides in its "P" or pertussis component or effect—although of course other components may be required as well.

DISCUSSION

It is clear from the first series of experiments that insulin given in a time limited intermittent fashion is capable of preventing diabetes—even when given relatively late in life. IGF1 given in a dose with an equivalent hypoglycaemic effect to the larger dose of insulin was completely ineffective. This implies that the protective effect of insulin lies not in its metabolic effects such as hypoglycaemia or growth promotion, but rather its antigenic effect. The principal protective antigenic site probably lies on the A chain, though it cannot be discounted that sites on the B-chain may also be effective to a lesser degree. Maclaren & Muir in their patent application (WO 94/23737) have reported their insulin B chain or a portion thereof but not A chain, given as a vaccine in combination with Freund's incomplete adjuvant (paraffin oil and mannide monooleate 85:15 ratio), protects NOD mice against diabetes. Freund's incomplete adjuvant is not licensed for human use. That application states that its inventors found "no protective effects [with the A chain] (IDD rate 53%) while all of the protection was localized to the B chain (IDD rate 16%)".

In our hands, the substantial protective effect of the A-chain could only be seen in combination with the DPT vaccine. The latter may have a non-specific adjuvant effect, but it cannot be discounted that the A-chain forms a hapten group with some component of the vaccine.

It was not the purpose of these experiments to demonstrate the way in which the protection occurred. Insulitis was not avoided in the animals which did not develop diabetes in any group, although obviously more had islet invasive infiltration in the groups which developed diabetes.

We also observed the acquisition of insulin antibodies in those animals treated with insulin but not the insulin fragments. It is likely however that the protection afforded by the insulin A chain in particular is a result of its interaction with the immune system—presumably targeting the B-cells of the islets in some specific way leading to at least partial maintenance of tolerance to these cells. See Miller et al (1992) Proc Natl. Acad. Sci. USA 89 421–425, Khoury et al (1992) J. Exp. Med. 176 1355–1364, and Karpus & Swanbord (1991) J. Immunol. 146 1163–1168.

Attempts to prevent Type 1 diabetes using substantial daily doses of insulin are already being undertaken. It is possible that a much less Draconian intervention using insulin A chain incorporated in routine schedules for immunisation against diphtheria tetanus and whooping cough could be effective, avoiding both the invasiveness of daily injections and the risk of hypoglycaemia.

VARIATIONS

Clearly, the most useful variation from the preferred embodiments described above is to apply the invention to humans instead of to the mouse model that has provided the information of the preferred embodiments on which this invention is based. Trials should be performed, in which the dose found effective in the mouse trials (which last about one year) is scaled up to an amount—and number of administrations—found to be effective yet safe in humans, while retaining a substantially similar composition. It will be appreciated that trials of this nature will be comparatively lengthy. Initially, doses will be at least partially determined by extrapolation from the above NOD mouse data.

Some detailed variations are:

In Regard to Insulin or Fragments Thereof

Entire insulin molecules in combination with the preferred adjuvant were substantially effective but that treatment carries the risk of adversely affecting the glucose regulation system of the recipient, so the invention preferably comprises an immunologically active but physiologically inactive fragment of the insulin molecule. The A chain in combination with an adjuvant according to this invention has been found to be effective while possibly fragments of the A chain, or fragments of the A chain together with fragments or all of the B chain will also be suitably effective. The species of origin of the A chain fragment may be varied. The source of the fragment may be any suitable manufacturing means, such as recovery from organs, recombinant production, or synthesis.

In Regard to Adjuvant

It appears that the choice of adjuvant is relevant to the degree of protection. Incomplete Freund's adjuvant was not successful in our trials in mice so it is presumed at this stage that the triple vaccine DPT or at least one component of the mixture is generally required. Quite possibly this component is the killed cells of the whooping cough bacterium. Equally possibly the other components of the triple vaccine aid in stimulating the immune system, and it is likely that at least a newly introduced quadruple vaccine (also including *Haemophilus influenzae* type b antigen) will be effective. Trials using other sources or types of vaccine may extend the range of suitable adjuvants beyond the known range.

In Regard to Timing

Although the second series of experiments attempted to mimic a human dosage strategy modelled on our orthodox immunization with triple vaccine, trials to establish an optimum combination of dose, age, and materials in humans may take a long time to complete as there may be a 30-month delay between administration and the possible appearance of antibodies which herald the risk of developing diabetes. Therefore we prefer to specify a treatment regime based on extrapolation from the NOD mouse model, while also including treatment regimes which vary widely from it. For example it is possible that booster doses may be needed from time to time in the much longer-lived human.

In Regard to Selection

One option is to select for treatment just those individuals with a close relative who has diabetes mellitus.

A related option is to select those individuals who, at a neonatal stage, have been shown to have a diabetes-related genotype.

Another option is to select for treatment those individuals who exhibit a raised titre of islet-cell antibodies. However it may be too late to treat such individuals by that time. One test that we use routinely is an indirect immunofluorescence test in which a titre of 10 units generally indicates an incidence of 10% of diabetes in the next 10 years, or an incidence of 20 units or more suggests an incidence of 50% in the next 7 years. It is however possible that a raised titre may indicate that the disease has already progressed too far for the prevention method of this invention to be successful.

A third option is to select all individuals passing through the age range for treatment with DPT or the like and in view of the limited ability to forecast diabetes and the expense of antibody tests or insulin treatment this may be the best option.

In Regard to Other Autoimmune Diseases

The basis of the invention—that inoculation with a protein (or at least a refinement of that inoculation) can subdue an autoimmune disease resulting in a disturbance of metabolism of that protein—may be applied to other autoimmune diseases, or diseases in which an autoimmune basis is suspected but not as yet proven. We have not clearly established whether other known interactions between pertussis vaccines and hormonal regulation of glucose by the islets are important in rendering the selected adjuvant successful in this preferred embodiment. Nevertheless this invention leads to the possibility that for example a demyelinating disease might be controlled with the same or a similar adjuvant and a myelin-associated protein.

ADVANTAGES

Advantages of the invention include the individual and population-wide benefits of minimising the incidence of diabetes mellitus which include aspects of suffering, medical treatment costs, and the like.

A further advantage is that the components of the treatment (particularly the adjuvant) are already well accepted as medication. The administered protein (A chain or variant) is simply a fragment of a widely present molecule and has not itself been altered by substitution of components. One's body continually produces a substantial amount of insulin A chain as one step of its degradation. The preferred adjuvant, triple vaccine (DPT) and the like is already widely used.

A yet further advantage is that no extra immunising injections are likely to be needed as the mixture of DPT and A chain may be supplied pre-mixed and suitably stabilised as a replacement for a standard DPT injection.

Finally, it will be appreciated that various alterations and modifications may be made to the foregoing without departing from the scope of this invention as set forth.

I claim:

1. A pharmaceutical composition for the treatment of a mammal at risk of developing diabetes consisting essentially of an effective amount of *Haemophilus pertussis* adjuvant and an effective amount of the A chain peptide of insulin.

2. The composition of claim 1, wherein the adjuvant comprises killed cells of *Haemophilus pertussis*.

3. The composition of claim 2, wherein the adjuvant also contains tetanus toxoid and diphtheria toxoid.

4. The composition of claim 1, wherein the adjuvant contains antigenic material from *Haemophilus influenza* type B.

5. A method for reducing the risk of developing diabetes in a mammal in need thereof comprising subcutaneously administering an effective amount of the pharmaceutical composition of claim 1.

6. The method of claim 5, wherein from 50 micrograms to 20 milligrams of A chain peptide is administered per dose.

7. The method of claim 6, wherein 10 milligrams of A chain peptide is administered per dose.

* * * * *